United States Patent
Nabi et al.

(10) Patent No.: US 6,730,310 B2
(45) Date of Patent: May 4, 2004

(54) WASH-OFF VITAMIN E COMPOSITIONS

(75) Inventors: Zeenat F. Nabi, Cranbury, NJ (US); Thomas Gregory Polefka, Somerset, NJ (US); Nadia Soliman, East Brunswick, NJ (US); Amir Tavakkol, Mountain Lakes, NJ (US)

(73) Assignee: Colgate-Palmolive Company, NY, NY (US)

( * ) Notice: Subject to any disclaimer, the term of this patent is extended or adjusted under 35 U.S.C. 154(b) by 0 days.

(21) Appl. No.: 09/902,314

(22) Filed: Jul. 10, 2001

(65) Prior Publication Data
US 2001/0051173 A1 Dec. 13, 2001

Related U.S. Application Data

(63) Continuation of application No. 09/542,480, filed on Apr. 3, 2000, which is a continuation-in-part of application No. 09/183,524, filed on Oct. 30, 1998, now Pat. No. 6,136,330, and a continuation-in-part of application No. 09/545,871, filed on Mar. 6, 2000, which is a continuation of application No. 09/182,932, filed on Oct. 30, 1998, now abandoned.

(51) Int. Cl.⁷ ................................. A61K 7/00
(52) U.S. Cl. ................ 424/401; 514/844; 514/858
(58) Field of Search ............... 424/401; 514/844, 514/458

(56) References Cited

U.S. PATENT DOCUMENTS

| | | | | |
|---|---|---|---|---|
| 4,551,332 A | * | 11/1985 | Stillman | 424/401 |
| 5,415,875 A | * | 5/1995 | Kakoki et al. | 424/581 |
| 5,565,189 A | | 10/1996 | Mulder | 424/43 |
| 5,573,756 A | | 11/1996 | Lambrechts | 424/70.24 |
| 5,593,682 A | | 1/1997 | Papas et al. | 424/401 |
| 5,741,496 A | | 4/1998 | Khaiat | 424/401 |
| 6,068,848 A | * | 5/2000 | Gubernick et al. | 424/401 |

FOREIGN PATENT DOCUMENTS

| | | | | |
|---|---|---|---|---|
| DE | 29607273 | 6/1996 | | |
| DE | 19710149 A1 | 9/1998 | | A61K/31/355 |
| EP | 0343694 A2 | 11/1989 | | A61K/31/355 |
| EP | 0353161 A1 | 1/1990 | | A61K/7/48 |
| EP | 0643960 A1 | 9/1994 | | A61K/7/48 |
| EP | WO98/05294 | 2/1998 | | A61K/7/00 |
| EP | WO98/40044 | 9/1998 | | A61K/7/00 |
| EP | WO99/13829 | 3/1999 | | A61K/7/06 |
| EP | 0964047 A1 | 12/1999 | | A61K/7/48 |
| EP | WO00/25738 | 5/2000 | | A61K/7/48 |
| EP | WO00/25739 | 5/2000 | | A61K/7/48 |
| FR | 2700954 | 8/1994 | | A61K/7/06 |
| JP | 58144311 A | 8/1983 | | A61K/7/00 |
| JP | 61143311 | 7/1986 | | A61K/7/00 |
| JP | 62-153208 | 7/1987 | | A61K/7/50 |
| JP | 62164609 | 7/1987 | | A61K/7/00 |
| JP | 1153623 A | 6/1989 | | G06F/3/033 |

OTHER PUBLICATIONS

Solid Lipid Nanoparticles (SLN/Lipopearls)—a pharmaceutical and cosmetic carrier for the application of vitamin E in dermal products; A. Dingler, RP Blum, H. Niehus, RH Muller, S. Gohla; Department of Pharmaceuticals, Biopharmaceutics and Biotechnology, Free University of Berlin, Germany; J. Microencapsul 1999 Nov.–Dec.; 16(6):751–67.
Free radicals and aging of the skin; I. Emerit; Free Radical Research Group, University of Paris V1, France; EXS 1992; 62:328–41.
Loss of Heterozygosity in MENI Skin Tumors; Celena Sun; The Journal of Investigative Dermatology, An International Journal for Research in Cutaneous Biology; April 1998/vol. 110/No. 4.
Protecting the Skin Against Exogenous Noxes; Thomas Forster, Jochen Meister, Hinrich Moller, Stephanie Ortanderl and Kordeela Schlotmann; Cosmetics & Toiletries; vol. 114, No. 3, Mar. 1999.
Skin Care Delivery Systems; Tom Branna; Happi, Mar. 2000; pp. 79–83.

* cited by examiner

*Primary Examiner*—Thurman K. Page
*Assistant Examiner*—Konata M George
(74) *Attorney, Agent, or Firm*—Martin Barancik; Rosemary M. Miano

(57) ABSTRACT

A topical composition suitable for application to skin comprising an amount of antioxidant action vitamin and vitamin precursor sufficient to bring about an effect selected from the group consisting of a level of vitamin on the skin significantly above the amount of vitamin on normal vitamin untreated skin for a period of treating four hours after application of the said vitamin containing composition, a reduction of lipid peroxide levels brought about by an insult to the skin wherein the skin is treated with the said vitamin containing composition prior to said insult, a level of skin vitamin which is significantly above the level of vitamin on the skin brought about by oral ingestion of the vitamin, or a combination of any of a, b, or c.

12 Claims, No Drawings

WASH-OFF VITAMIN E COMPOSITIONS

This is a continuation of pending prior application Ser. No. 09/542,480 filed Apr. 3, 2000, which is a continuation-in-part of U.S. Ser. No. 09/183,524 filed Oct. 30, 1998, now U.S. Pat. No. 6,136,330 and a continuation-in-part of pending U.S. Ser. No. 09/545,871 filed Mar. 6, 2000 which is a continuation of U.S. Ser. No. 09/182,932 filed Oct. 30, 1998, now abandoned, all of which applications are incorported herein by reference.

BACKGROUND OF THE INVENTION

Vitamins are a well-known significant portion of a person's diet. Their importance in nutrition has been known for many years. It is only relatively recently that their role in the body's defense mechanism(s) against various insults, particularly oxidation reactions, has become more appreciated. Their role as a protecting antioxidant, particularly Vitamin E, is now becoming more understood. Vitamins in general have been broadly disclosed as optional ingredients in skin care and skin cleansing compositions. However, obtaining significant deposition of vitamins, particularly Vitamin E, upon human skin has been difficult so far. This may be due to the fact that the combination of solubilization to obtain a stable composition and thereafter depositing vitamins on the skin is potentially contradictory. Additionally it is thought that Vitamin E, per se, is unstable. Without appropriate skin deposition of the vitamin, it has not been altogether possible to measure such parameters as the endurance of deposited vitamins on skin, the value of deposited vitamins on skin with respect to the neutralization of oxidants on skin, and the deposition of vitamins from a topical skin composition, particularly a rinse off skin cleansing composition, in comparison to skin vitamin levels occurring from orally administered vitamins.

We have now found that a composition containing both Vitamin E and Vitamin E precursor, such as Vitamin E acetate, deposits relatively large quantities of Vitamin E on the skin and maintains significant quantities of Vitamin E on the skin for at least fifteen (15) hours and up to twenty four (24) hours, or even more, after rinsing off the composition. Additionally, the presence of Vitamin E through such skin deposition brings a lowering of lipid peroxide values when skin is exposed to an insult which results in the raising of lipid peroxide values, thus providing a benefit to the skin. Still further, the usage of topical application of vitamins, particularly Vitamin E, to the skin results in a significantly higher skin level of vitamins compared to the level of vitamin achieved by oral ingestion of such vitamin.

SUMMARY OF THE INVENTION

A topical composition suitable for application to skin comprising an antioxidant active amount of vitamin and vitamin precursor sufficient to bring about an effect selected from the group consisting of a. a level of vitamin on the skin significantly above the amount of vitamin on vitamin untreated skin for a period of at least about fifteen hours after application of the said vitamin containing topical composition, b. a reduction of lipid peroxide levels brought about by an insult to the skin wherein the skin is treated with the said vitamin containing composition prior to said insult, c. a level of skin vitamin which is significantly above the level of skin vitamin brought about by oral ingestion of the vitamin, or d. a combination of any of a, b, or c.

Various aspects within the invention scope are combination of the Vitamin E and Vitamin E precursor, particularly esters of Vitamin E such as the methyl ester, in the composition; the usage of a solid or liquid, including gel, composition which is a rinse off composition as opposed to a leave on composition, such as a lotion, cream or ointment; the combination of the inventive composition with an effective level of skin cleansing surfactant; the usage of quite low levels of vitamin and vitamin precursor to obtain the effects which are observed; the raising of lipid peroxide levels in skin through environmental insults such as exposure to ozone and other known oxidizers such as peroxides, for example cumene hydroperoxide, which can be at least partially overcome by effective levels of pre-deposited vitamin; obtaining a higher skin level of vitamin through topical deposition than occurs through oral ingestion of vitamin, said oral ingestion at a level which is thirteen times the recommended daily dietary vitamin dosage.

A further desirable effect of the invention is the composition further comprising a composition stabilizing effective amount of a cationic polymer.

DETAILED DESCRIPTION OF INVENTION

The observed effects of vitamin deposition on skin from this invention are significant. The vitamins, which are employed, are the ones usually associated with antioxidant activity, for example Vitamin A, C, and E; particularly Vitamin E. Also present in the topical composition is a precursor of the vitamin. A precursor of the vitamin is a material converted to the respective vitamin when the precursor is contacted with skin. More than one vitamin, a vitamin and a precursor, or precursor can be present in the composition. Examples of precursors are esters of Vitamins A and E, such as esters having one to about twenty carbon atoms. Examples of effective esters are those having about 1 to about 20 carbon atoms, for example, the methyl, propyl, hexyl, decyl, lauryl, palmityl and behenyl ester of the vitamin such as the methyl ester of Vitamin E or the palmitate ester of Vitamin A. Of the actual vitamin the alpha tocopherol compound is preferred as Vitamin E. Similar precursors can be used for Vitamin C. Retinyl palmitate is the preferred precursor for Vitamin A. Vitamin E methyl ester (Vitamin E acetate) is the preferred precursor for Vitamin E. The fact that Vitamin E precursor is so effective in the compositions is suprising because it is inactive per se and should be converted to Vitamin E for antioxidant activity. However, a recent article indicates that skin does not have the appropriate system(s) to convert Vitamin E ester, particularly methyl ester to Vitamin E: *Alberts et al, Nutrition and Cancer,* 1996, pages 193–201.

The quantity of vitamin and vitamin precursor in the compositions is that amount sufficient to bring about at least one of the effects a, b, and c enumerated above. Generally the quantity of vitamin is a minimum of about 0.005 wt % of the composition, desirably a minimum of about 0.01, 0.05, or 0.1 wt % of the composition. The maximum quantity of vitamin is determined somewhat by the stability of the composition in which it resides. Generally no more than about 3 wt % of the composition is desirably used, more desirably no more than about 2, 1 or 0.5 wt %. With respect to vitamin precursor, generally a minimum of about 0.002 wt % of the composition is used, desirably a minimum of about 0.04, 0.02, or 0.03 wt % of the composition. The maximum of vitamin precursor is determined somewhat by the stability of the composition which it resides. Generally, no more than about 9 wt % of the composition is desirably used, more desirably no more than about 6, 3 or 1.5 wt %.

A wt % ratio of vitamin to vitamin precursor, particularly Vitamin E, is from about 1 to about 3 to about 3 to about 1.

In this invention system, the cationic polymer assists in stabilizing the system. Without the cationic polymer the vitamins in a substantially aqueous system, Preparation 1 below but without cationic agent, rise to the top of the liquid as a visible mass. With the cationic deposition agent Preparation 1 is obtained as a visually homogenous mass.

Cationic polymers are that generic class of materials, which generally provide a positive skin feel to the skin during cleansing application, rinse off, and thereafter.

Cationic polymers includes but are not limited to the following groups:
 (I) cationic polysaccharides;
 (II) cationic copolymers of saccharides and synthetic cationic monomers, and
 (III) synthetic polymers selected from the group consisting of:
  (a) cationic polyalkylene imines
  (b) cationic ethoxy polyalkylene imines
  (c) cationic poly[N-[3-(dimethylammonio)propyl]-N' [3-(ethyleneoxyethylene dimethylammonio)propyl] urea dichloride]
  (d) in general a polymer having a quaternary ammonium or substituted ammonium ion.

The cationic polysaccharide class encompasses those polymers based on 5 or 6 carbon sugars and derivatives, which have been made cationic by engrafting of cationic moieties onto the polysaccharide backbone. They may be composed of one type of sugar or of more than one type, i.e. copolymers of the above derivatives and cationic materials. The monomers may be in straight chain or branched chain geometric arrangements. Cationic polysaccharide polymers include the following: cationic celluloses and hydroxyethylcelluloses; cationic starches and hydroxyalkyl starches; cationic polymers based on arabinose monomers such as those which could be derived from arabinose vegetable gums; cationic polymers derived from xylose polymers found in materials such as wood, straw, cottonseed hulls, and corn cobs; cationic polymers derived from fucose polymers found as a component of cell walls in seaweed; cationic polymers derived from fructose polymers such as Inulin found in certain plants; cationic polymers based on acid-containing sugars such as galacturonic acid and glucuronic acid; cationic polymers based on amine sugars such as galactosamine and glucosamine; cationic polymers based on 5 and 6 membered ring polyalcohols; cationic polymers based on galactose monomers which occur in plant gums and mucilages; cationic polymers based on mannose monomers such as those found in plants, yeasts, and red algae; cationic polymers based on galactommannan copolymer known as guar gum obtained from the endosperm of the guar bean.

Specific examples of members of the cationic polysaccharide class include the cationic hydroxyethyl cellulose JR 400 made by Union Carbide Corporation; the cationic starches Stalok® 100, 200, 300, and 400 made by Staley, Inc.; the cationic galactomarnans based on guar gum of the Galactasol 800 series by Henkel, Inc. and the Jaguar Series by Celanese Corporation.

The cationic copolymers of saccharides and synthetic cationic monomers useful in the present invention encompass those containing the following saccharides: glucose, galactose, mannose, arabinose, xylose, fucose, fructose, glucosamine, galactosamine, glucuronic acid, galacturonic acid, and 5 or 6 membered ring polyalcohols. Also included are hydroxymethyl, hydroxyethyl and hydroxypropyl derivatives of the above sugars. When saccharides are bonded to each other in the copolymers, they may be bonded via any of several arrangements, such as 1,4-α; 1,4-β; 1,3-α; 1,3-β and 1,6 linkages. The synthetic cationic monomers for use in these copolymers can include dimethyldiallylammonium chloride, dimethylaminoethylmethyacrylate, diethyldiallylarnmonium chloride, N,N-diallyl,N-N-dialklyl ammonium halides, and the like. A preferred cationic polymer is Polyquaternium 7 prepared with dimethyldiallylammonium chloride and acrylamide monomers.

Examples of members of the class of copolymers of saccharides and synthetic cationic monomers include those composed of cellulose derivatives (e.g. hydroxyethyl cellulose) and N,N-diallyl,N-N-dialkyl ammonium chloride available from National Starch Corporation under the tradename Celquat.

Further cationic synthetic polymers useful in the present invention are cationic polyalkylene imines, ethoxypolyalkelene imines, and poly{N-[3-(dimethylammonio)propyl]-N'-[3-(ethyleneoxyethylene dimethylammoniumo)propyl]urea dichloride] the latter of which is available form Miranol Chemical Company, Inc. under the trademark of Miranol A-15, CAS Reg. No. 68555-336-2. Preferred cationic polymeric skin conditioning agents of the present invention are those cationic polysaccharides of the cationic guar gum class with molecular weights of 1,000 to 3,000,000. More preferred molecular weights are from 2,500 to 350,000. These polymers have a polysaccharide backbone comprised of galactomannan units and a degree of cationic substitution ranging from about 0.04 per anydroglucose unit to about 0.80 per anydroglucose unit with the substituent cationic group being the adduct of 2,3-epoxypropyl-trimethyl ammonium chloride to the natural polysaccharide backbone. Examples are JAGUAR C-14-S, C-15 and C-17 sold by Celanese Corporation, which trade literature reports have 1% viscosities of from 125 cps to about 3500±500 cps.

Still further examples of cationic polymers include the polymerized materials such as certain quaternary ammonium salts, copolymers of various materials such as hydroxyethyl cellulose and dialkyldimethyl ammonium chloride, acrylamide and beta methacryloxyethyl trimethyl ammonium methosulfate, the quaternary ammonium salt of methyl and stearyl dimethylaminoethyl methacrylate quaternized with dimethyl sulfate, quaternary ammonium polymer formed by the reaction of diethyl sulfate, a copolymer of vinylpyrrolidone and dimethyl aminoethylnethacrylate, quaternized guars and guar gums and the like. Exemplary of cationic polymers which can be used to make the complexes of this invention include, as disclosed in the CTFA International Cosmetic Ingredient Dictionary (Fourth Edition, 1991, pages 461–464); Polyquaternium-1, -2, -4 (a copolymer of hydroxyethylcellulose and diallyldimethyl ammonium chloride), -5 (the copolymer of acrylamide and beta-methacrylyloxyethyl trimethyl ammonium methosulfate), -6 (a polymer of dimethyl diallyl ammonium chloride), -7 (the polymeric quaternary ammonium salt of acrylamide and dimethyl diallyl ammonium chloride monomers), -8 (the polymeric quaternary ammonium salt of methyl and stearyl dimethylaminoethyl methacrylate quaternized with dimethyl sulfate), -9 (the polymeric quaternary ammonium salt of polydimethylaminoethyl methacrylate quaternized with methyl bromide), -10 (a polymeric quaternary ammonium salt of hydroxyethyl cellulose reacted with a trimethyl ammonium substituted epoxide), -11 (a quaternary ammonium polymer formed by the reaction of diethyl sulfate and a copolymer of vinyl pyrrolidone and dimethyl aminoethylmethacrylate), -12 (a polymeric quaternary ammonium salt prepared by the reaction of ethyl methacrylate/abietyl methacrylate/diethylaminoethyl methacrylate copolymer with dimethyl sulfate), -13 (a polymeric quaternary ammonium salt prepared by the reaction of ethyl methacrylate/oleyl methacrylate/diethylaminoethyl methacrylate copolymer with dimethyl sulfate), -14, -15 (the copolymer of acrylamide and betamethacryloxyethyl trimethyl ammonium chloride), -16 (a polymeric quaternary ammonium salt formed from methylvinylimidazolium chloride and vinylpyrrolidone), -17, -18, -19 (polymeric quaternary ammonium salt prepared by the reaction of polyvinyl alcohol with 2,3-epoxy-propylamine), -20 (the polymeric quaternary ammonium salt prepared by the reaction of polyvinyl octadecyl ether with 2,3-epoxypropylamine), -22, -24 a polymeric quaternary ammonium salt of hydroxyethyl cellulose reacted with a lauryl dimethyl ammonium substituted epoxide), -27 (the block copolymer formed by the reaction of Polyquaternium-2 (q.v.) with Polyquaternium-17 (q.v.)), -28, -29 (is Chitosan (q.v.) that has been reacted with propylene oxide and quaternized with epichlorohydrin), and -30.

Generally the cationic deposition agent is a minimum of about 0.01, more desirably a minimum of about 0.03, 0.1 or 0.2 wt % of the composition. The maximum quantity of the cationic agent is generally determined by its effects on viscosity, stickiness and general sensory perceptions of the composition user. Generally, no more than about 2 wt %, desirably no more than about 1.5, 1 or 0.8 wt % of the composition need be employed as a cationic deposition agent.

Any composition, which can be applied topically to the skin, can be employed in this invention. Examples of such compositions includes solids such as soap bars, combars, syndet bars, and liquids including gels such as solutions, suspensions, emulsions, lotions, creams, ointments, salves, and the like, Surprisingly, effects of the composition are obtained with rinse off compositions such as solids (bars) and liquids, including gels such as hand and face cleansers, shower gels, body cleansers, and the like. Such cleansing compositions are characterized by having a cleansing effective amount of at least one surfactant present in the composition. There must be at least one surfactant present in the composition. The surfactant can be anionic, nonionic, amphoteric, or cationic, preferably anionic. Soap, a long chain alkyl or alkenyl, branched or normal carboxylic acid salt such as sodium, potassium, ammonium or substituted ammonium salt can be present in the composition as an example of an anionic surfactant. Exemplary of long chain allyl or alkenyl are from about 8 to about 22 carbon atoms in length, specifically about 10 to about 20 carbon atoms in length, more specifically alkyl and most specifically normal, or normal with little branching. Small quantities of olefinic bond(s) may be present in the predominantly alkyl sections, particularly if the source of the "alkyl" group is obtained from a natural product such as tallow, coconut oil and the like. Because of its potential harshness soap is not a preferred surfactant and can be omitted from the composition unless a soap-containing bar is employed or mildness increasing corrections are employed.

Other surfactants can be present in the composition as well. Examples of such surfactants are the anionic, amphoteric, nonionic and cationic surfactants. Examples of anionic surfactants include but are not limited to soaps, alkyl sulfates, anionic acyl sarcosinates, methyl acyl taurates, N-acyl glutamates, acyl isethionates, alkyl sulfosuccinates, alkyl phosphate esters, ethoxylated alkyl phosphate esters, trideceth sulfates, protein condensates, mixtures of ethoxylated alkyl sulfates and the like.

Alkyl chains for these surfactants are $C_8$–$C_{22}$, preferably $C_{10}$–$C_{18}$, more preferably $C_{12}$–$C_{14}$.

Anionic non-soap surfactants can be exemplified by the alkali metal salts of organic sulfate having in their molecular structure an alkyl radical containing from about 8 to about 22 carbon atoms and a sulfonic acid or sulfuric acid ester radical (included in the term alkyl is the alkyl portion of higher acyl radicals). Preferred are the sodium, ammonium, potassium or triethanolamine alkyl sulfates, especially those obtained by sulfating the higher alcohols ($C_8$–$C_{18}$ carbon atoms), sodium coconut oil fatty acid monoglyceride sulfates and sulfonates; sodium or potassium salts of sulfuric acid esters of the reaction product of 1 mole of a higher fatty alcohol (e.g., tallow or coconut oil alcohols) and 1 to 12 moles of ethylene oxide; sodium or potassium salts of alkyl phenol ethylene oxide ether sulfate with 1 to 10 units of ethylene oxide per molecule and in which the alkyl radicals contain from 8 to 12 carbon atoms, sodium alkyl glyceryl ether sulfonates; the reaction product of fatty acids having from 10 to 22 carbon atoms esterified with isethionic acid and neutralized with sodium hydroxide; water soluble salts of condensation products of fatty acids with sarcosine; and others known in the art.

Zwitterionic surfactants can be exemplified by those which can be broadly described as derivatives of aliphatic quaternary ammonium, phosphonium, and sulfonium compounds, in which the aliphatic radicals can be straight chain or branched and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

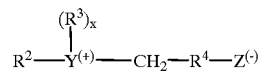

wherein $R^2$ contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; R3 is an alkyl or monohydroxyalkyl group containing 1 to about 3 carbon atoms; X is 1 when Y is a sulfur atom and 2 when Y is a nitrogen or phosphorus atom, $R^4$ is an alkylene or hydroxyalkylene of from 0 to about 4 carbon atoms and Z is a radical selected from the group consisting of carboxylate, sulfonate, sulfate, phosphonate, and phosphate groups.

Examples include: 4-[N,N-di(2-hydroxyethyl)-N-octadecylammonio]-butane-1-carboxylate; 5-[S-3-hydroxypropyl-S-hexadecylsulfonio]-3 hydroxypentane-1-sulfate; 3-[P,P-P-diethyl-P 3,6,9 trioxatetradecyl-phosphonio]-2-hydroxypropane-1-phosphate; 3-[N,N-dipropyl-N-3 dodecoxy-2-hydroxypropylammonio]-propane-1-phosphonate; 3-(N,N-di-methyl-N-hexadecylammonio) propane-1-sulfonate; 3-(N,N-dimethyl-N-hexadecylammonio)-2-hydroxypropane-1-sulfonate; 4-(N,N-di(2-hydroxyethyl)-N-(2 hydroxydodecyl) ammonio]-butane-1-carboxylate; 3-[S-ethyl-S-(3-dodecoxy-2-hydroxypropyl)sulfonio]-propane-1-phosphate; 3-(P,P-dimethyl-P-dodecylphosphonio)propane-1-phosphonate; and 5-[N,N-di(3-hydroxypropyl)-N-hexadecylammonio]-2-hydroxy-pentane-1-sulfate.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate, N-alkyltaurines, such as the one prepared by reacting dodecylamine with sodium isethionate according to the teaching of U.S. Pat. No. 2,658,072, N-higher alkyl aspartic acids, such as those produced according to the teaching of U.S. Pat. No. 2,438,091, and the products sold under the trade name "Miranol" and described in U.S. Pat. No. 2,528,378. Other amphoterics such as betaines are also useful in the present composition.

Examples of betaines useful herein include the high alkyl betaines such as coco dimethyl carboxymethyl betaine, lauryl dimethyl carboxy-methyl betaine, lauryl dimethyl alpha-carboxyethyl betaine, cetyl dimethyl carboxymethyl betaine, lauryl bis-(2-hydroxyethyl)carboxy methyl betaine, stearyl bis-(2-hydroxypropyl) carboxymethyl betaine, oleyl dimethyl gamma-carboxypropyl betaine, lauryl bis-(2-hydro-xypropyl) alpha-carboxyethyl betaine, etc. The sulfobetaines may be represented by coco dimethyl sulfopropyl betaine, stearyl dimethyl sulfopropyl betaine, amido betaines, amidosulfobetaines, and the like.

Many cationic surfactants are known to the art. By way of example, the following may be mentioned:

stearyldimenthylbenzyl ammonium chloride;
dodecyltrimethylammonium chloride;
nonylbenzylethyldimethyl ammonium nitrate;
tetradecylpyridinium bromide;
laurylpyridinium chloride;
cetylpyridinium chloride
laurylpyridinium chloride;
laurylisoquinolium bromide;
ditallow(Hydrogenated)dimethyl ammonium chloride;
dilauryldimethyl ammonium chloride; and
stearalkonium chloride.

Additional cationic surfactants are disclosed in U.S. Pat. No. 4,303,543 see column 4, lines 58 and column 5, lines 1–42, incorporated herein by references. Also see CTFA Cosmetic Ingredient Dictionary, 4th Edition 1991, pages 509–514 for various long chain alkyl cationic surfactants; incorporated herein by references.

Nonionic surfactants can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration with ethylene oxide, e.g., a coconut alcohol ethylene oxide condensate having from 10 to 30 moles of ethylene oxide per mole of coconut alcohol, the coconut alcohol fraction having from 10 to 14 carbon atoms. Other ethylene oxide condensation products are ethoxylated fatty acid esters of polyhydric alcohols (e.g., Tween 20-polyoxyethylene (20) sorbitan monolaurate).

4. Long chain tertiary amine oxides corresponding to the following general formula:

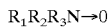

wherein $R_1$ contains an alkyl, alkenyl or monohydroxy alkyl radical of from about 8 to about 18 carbon atoms, from 0 to about 10 ethylene oxide moieties, and from 0 to 1 glyceryl moiety, and, $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyldodecylamine oxide, oleyl-di(2-hydroxyethyl) amine oxide, dimethyloctylamine oxide, dimethyldecylamine oxide, dimethyltetradecylamine oxide, 3,6,9 trioxaheptadecyldiethylamine oxide, di(2-hydroxyethyl)-tetradecylamine oxide, 2-dodecoxyethyl-dimethylamine oxide, 3-dodecoxy-2-hydroxypropyldi(3-hydroxypropyl)amine oxide, dimethylhexadecylamine oxide.

5. Long chain tertiary phosphine oxides corresponding to the following general formula:

wherein R contains an alkyl, alkenyl or monohydroxyalkyl radical ranging from 8 to 20 carbon atoms in chain length, from 0 to about 10 ethylene oxide moieties and from 0 to 1 glyceryl moiety and R' and R" are each alkyl or monohydroxyalkyl groups containing from 1 to 3 carbon atoms. The arrow in the formula is a conventional representation of a semipolar bond. Examples of suitable phosphine oxides are: dodecyldimethylphosphine oxide, tetradecylmethylethylphosphine oxide, 3,6,9-trioxaoctadecyldimethylphosphine oxide, cetyldimethylphosphine oxide, 3-dodecoxy-2-hydroxypropyldi(2-hydroxyethyl) phosphine oxide stearyldimethylphosphine oxide, cetylethyl propylphosphine oxide, oleyldiethylphosphine oxide, dodecyldiethylphosphine oxide, tetradecyldiethylphosphine oxide, dodecyldipropylphosphine oxide, dodecyldi(hydroxymethyl) phosphine oxide, dodecyldi(2-hydroxyethyl)phosphine oxide, tetradecylmethyl-2-hydroxypropylphosphine oxide, oleyldimethylphosphine oxide, 2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contain alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include: octadecyl methyl sulfoxide, 2-ketotridecyl methyl sulfoxide, 3,6,9-trioxaoctadecyl 2-hydroxyethyl sulfoxide, dodecyl methyl sulfoxide, oleyl 3-hydroxypropyl sulfoxide, tetradecyl methyl sulfoxide, 3 methoxytridecylmethyl sulfoxide, 3-hydroxytridecyl methyl sulfoxide, 3-hydroxy-4-dodecoxybutyl methyl sulfoxide.

7. Alkylated polyglycosides wherein the alkyl group is from about 8 to about 20 carbon atoms, preferably about 10 to about 18 carbon atoms and the degree of polymerization of the glycoside is from about 1 to about 3, preferably about 1.3 to about 2.0.

For solid compositions such as bars, there is generally at least about 30 wt % surfactant, desirably 40, 50, 60 or 70 wt % with desirably at least some soap present although soap free bars can be prepared. Usually there is no more than about 95 wt % surfactant therein, desirably nor more than about 90, 85, 80, or 75 wt % surfactant. With reference to a non-solid composition, the amount of surfactant should generally be sufficient to exert a cleansing effect upon skin. Generally, a minimum of about 1 wt % of the composition can be a surfactant or mixtures thereof. Preferably about 2, 3, 4 or 5 wt % can be employed as a minimum. A maximum of about 30 wt % of the composition can be a surfactant or mixture thereof; preferably a maximum of about 25, 20 or 18 wt % can be employed. Generally for a rinse off, non-solid cleansing composition, the quantity of water is from about 70 to about 95 wt % of the composition. Desirably no more than about 90 wt % of the composition is water. A minimum of about 70 or 75 wt % of water can be employed.

A solid composition is generally at least about 10 wt % anionic surfactant of the total surfactant, desirably about 20, 30, or 40 wt % minimum anionic surfactant. A soap bar is essentially, 95% or greater soap as measured by wt % of total surfactant. The quantity of water in the solid is a minimum of about 4, 6 or 8 wt % of the composition. Generally no more than about 25 wt % desirably about 20, 18 or 15 wt % can be employed.

The compositions of the invention are prepared utilizing standard techniques in the art.

Below are typical formulations:

Preparation 1
Liquid Cleansing Composition

| Component | Wt % |
|---|---|
| Sodium Laureth Sulfate | 8 |
| Cocoamidiopropybetaine | 3 |
| Laurylpolyglucose | 1.1 |
| Ethylene Glycol Distearate | 0.25 |
| Sodium Chloride | 0.9 |
| Polyquat-7 | 0.2 |
| Glycerin | 0.2 |
| Tocopherol | 0.15 |
| Tocopheryl acetate | 0.1 |
| Laureth-4 | 0.1 |
| Citric Acid | 0.07 |
| Poloxamer 124 | 0.02 |
| Retinyl palmitate | 0.01 |
| Sodium Ascorbyl phosphate | 0.008 |
| Colorant, chelant, preservative and perfume | 1.3 |
| Water | Balance |

Note in this formulation precursors of Vitamin A and C are also present in small quantities.

Preparation 1

| COMPONENT | % Wt. |
|---|---|
| White Mineral Oil - Light | 4.0 |
| 99.5% Glycerin - USP | 2.0 |
| Isohexadecane | 1.5 |
| Glyceryl/PEG-100 Stearate Mixture | 2.0 |
| Isopropyl Palmitate | 1.5 |
| Snow White Petrolatum | 1.25 |
| Stearic Acid - Grade A | 1.0 |
| Cetyl-Stearyl Alcohol 50—50 | 1.0 |
| Tocopheryl Acetate | 1.0 |
| Silicone-350 CS | 1.0 |
| D-Panthenol | 0.5 |
| Tocopherol | 0.5 |
| Preservative Thickener, Chelator Gum, Perfume | 1.6 |
| Water | Balance |

The presence of a cationic deposition polymer surprisingly provides the additional benefit of stabilizing the topical composition of this invention. Without a compatibilization of the vitamin and precursor with the composition, appropriate and consistent deposition levels of the vitamin and precursor are more difficult to obtain.

In a standard shower gel of 8.6 wt % sodium laureth-2-sulfate, 3 wt % cocoamidopropylbetaine 1.125 wt % decylpolyglycoside, dp of about 1.5 as well as thickening agent sodium chloride of 0.87 wt %, the remainder of the composition being essentially water, there is added 0.15 wt % of Vitamin E and the following components (all wt % based on total composition). The vitamin solubility is visually evaluated in the table below.

| Expt | Polyquat-7, wt % | EGDS*, wt % | Vitamin E Acetate, wt % | Visual Evaluation |
|---|---|---|---|---|
| 1 | 0.2 | — | 0.1 | Vitamin soluble and homogenous, batch translucent |
| 2 | 0.2 | 0.25 | 0.1 | Vitamin soluble and homogenous |
| 3 | 0.2 | — | 0.5 | Vitamin soluble and homogenous |
| 4 | 0.2 | 0.25 | 0.5 | Vitamin soluble and homogenous |
| 5 | — | — | 0.1 | Very slight white rim. Batch translucent |
| 6 | — | 0.25 | 0.1 | Very slight white rim. |
| 7 | — | — | 0.5 | White rim on surface. |
| 8 | — | 0.25 | 0.5 | White rim on surface which can be seen with pearlescent present |

*Ethylene glycol distearate

As is observed, the cationic polymer brings about visual homogenity to the formulation. It is believed that a stable emulsion is formed.

The compositions of the invention provide significant effects including prolonged presence on the skin, antioxidant action, and substantial quantitative presence as measured by skin deposits compared to skin deposits of vitamins present from large quantities of vitamins administered orally. In this manner, these compositions can provide substantial protective benefits and advantages to skin, particularly human skin.

Below are the experiments showing the effect(s) of these compositions.

Long Term Duration of Vitamin E Skin Deposition

Preparation 1 is Utilized in this Test

A. Twelve (12) female Caucasian volunteers between the ages of 18 and 55 are recruited so that ten panelists complete the study. The composition employed is the same as that of preparation 1 except that there is no sodium ascorbylphosphate.

The product is applied to three (3) skin sites. The fourth site is left untreated to serve as control. The time points and the untreated control site are randomized within panelists' forearms.

Subjects are allowed to continue with their normal bathing/shower routine prior to the study but are required to use the body-cleansing produce (vehicle containing no vitamins) provided to them for daily shower/bath and hand washing. They are instructed not to use any cosmetics or moisturizers on their arms starting seven days prior to the start of the study and throughout the study.

On the first day of the study according to a pre-determined schedule, the panelists' forearms are inspected by a clinician for any visible skin anomaly. Using a marker pen, a technician delineates four square areas (approximately 5×5 cm) on each forearm separated equidistantly from each other. These markings specify the area to be subsequently washed with products. The technician then marks a square area (approx. 3×3 cm) inside each 5×5-cm areas. The smaller inner areas are used for ethanol extraction.

Next, one (1) of the predetermined sites is extracted with ethanol for biochemical analysis of baseline Vitamin E and Vitamin E acetate. Using a syringe, 0.4 ml (approx.: 0.4 g) of the bodywash is placed onto a wetted-gloved hand and used to gently massage (lather) the appropriate site(s) on the appropriate forearm(s) for 1 minute. The sites are rinsed under running water (95° F.) for 15–20 seconds and allowed to air dry for 1–2 minutes. There is only a single wash with the product.

At approximately 2 hours after the washing, one (1) of the sites is extracted with ethanol as described below. Ethanol extraction is repeated on a second site at 6 hours post washing. Panelists are allowed to leave the test facility between the $2^{nd}$ and $6^{th}$ hours of skin sampling (ethanol extraction). During this time, panelists are not allowed to stay in the sun, do yard work or in any way expose their forearms to the sun. On day 2, approximately 24 hours after the initial product application. The last remaining treated site is extracted as before. Panelists are not permitted to wash their forearms, tale a bath, shower, and swim, or in any way wet their forearms during the test period time.

B. Biochemical Analysis

After wiping the site, a technician places a 7.5 cm² glass cup on the topically treated sites and applies 1 ml of ethanol into the cup. Using a glass rod the skin is gently rubbed for 1 minute and the ethanolic extract is transferred into a vial. This is repeated for 4 times, samples pooled and dried under nitrogen for HPLC analysis.

C. Statistical Analyses

The significance of differences between various treatments is determined using two-way ANOVA and paired t-test at the 5% significance level.

D. Results

TABLE 1

| Duration in hours from Treatment Time | Vitamin E picomoles/cm² Skin mean ± standard error |
| --- | --- |
| 0 (untreated control) | 38 ± 15 |
| 2 | 172 ± 17 |
| 6 | 136 ± 7 |
| 24 | 94 ± 17 |

$P \leq 0.05$

As can be seen from these results, 24 hours after treatment, Vitamin E levels remain approximately 150% higher than untreated control skin. This shows the availability of Vitamin E essentially immediately and for up to 24 hours (p=0.007). Although it is not totally understood why deposited Vitamin E is so long lasting in skin, the measurements of the provitamin E (Vitamin E acetate) are of interest. These quantities according to time from application to skin are shown below:

TABLE 2

| Duration in hours from Treatment Time | Provitamin E Picomoles/cm² Skin mean ± standard error |
| --- | --- |
| 0 (untreated control) | 86 ± 35 |
| 2 | 235 ± 5 |
| 6 | 198 ± 34 |

There is no significant difference in provitamin E levels at 24 hours versus untreated control.

A study applying only Vitamin E acetate to skin explant tissue shows the generation of Vitamin E after a short induction period of less than three hours from time of application.

The combination of provitamin and vitamin result in substantially more vitamin measured in skin after at least 6 hours and up to at least about 24 hours, as well as giving significant levels essentially immediately after application.

Inhibition of Induced Lipid Hydroperoxide in Human Skin by Predeposit of Vitamin Antioxidant The composition used in the test procedure has 0.25 wt % Vitamin E and 0.1 wt % Vitamin E acetate. The formulation is otherwise the same as Preparation 1.

A. Test Procedure

Ten (10) female Caucasian volunteers between the ages of 18 and 55 are recruited so that nine (9) panelists complete the study.

The study is a randomized, between treatment and within-subject comparison where each panelist (n=9) has their left or right forearms exposed for 1 hour on four consecutive days to either air containing 0.8±0.04 ppm ozone, or to air alone. This level of ozone is a concentration, which can be found in urban smog levels. Prior to ozone exposure, randomly determined sites on forearms are washed with the shower gel containing 0.25% Vitamin E/0.1% Vitamin E acetate or its vehicle. Skin sampling is done at baseline prior to treatment and exposure, and then upon termination of the study on day 4. The data for lipid hydroperoxide (LPO) are derived from eight samples and measured by using Kamiya LPO-CC assay kit.

The significance of differences between various treatments and exposure is determined at the 5% significance level, by paired t-test and Analysis of Variance using JMP® statistical software.

On day 1, skin sites on each forearm are tape stripped to serve for baseline LPO levels. Prior to ozone exposure, appropriate sites on the forearms are washed (1×) for 1 minute with Vitamin E shower gel or its vehicle; the products remain on the sites for 1 minute after which they are rinsed off. Both forearms are washed simultaneously with the products. After drying, ethanol is used to extract Vitamin E from the stratum corneum whereas tape stripping is used to recover LPO for subsequent biochemical analyses, 3M Tape 480.

Clinical assessments are made by a trained evaluator using standardized scales of erythema, skin dryness, and edema prior to beginning of the study, during the study, and then 24 hours after tape stripping/ethanol extraction (day 5). The scores are not used to evaluate skin changes since the purpose of the clinical assessment is only to ensure that any unexpected events are recorded.

Results

Vitamin E levels in skin after a single wash with the composition.

TABLE 3

| Single Wash | Vitamin E Picomoles/cm$^2$ Skin mean ± standard error |
|---|---|
| Vehicle | 105 ± 36 |
| Test Composition with Vitamin E and Vitamin E acetate | 495 ± 79 |

Exposure to ozone reduces the amount of Vitamin E measured in skin after vitamin containing composition deposition but this level still remains 230% higher than skin which is only treated by vehicle alone, see below.

TABLE 4

Amount of Vitamin E in skin after Exposure

| | Vitamin E Picomoles/cm$^2$ Skin mean ± standard error |
|---|---|
| Vehicle, air exposed control | 105 ± 36 |
| Composition with Vitamin E and Vitamin E acetate, air exposed | 495 ± 79 |
| Composition with Vitamin E and Vitamin E acetate, ozone exposed | 346 ± 73 |

However, the predeposited Vitamin E is able to reduce the quantity of LPO produced by ozone exposure by approximately 30%, see below.

TABLE 5

LPO Levels for Vitamin treated vs. untreated Skin after Ozone Exposure

| | LPO nanomoles/cm$^2$ ± standard error |
|---|---|
| Untreated | 3.05 ± .84 |
| Composition Treated | 2.1 ± .91 |

Using human skin ex vivo system and the same composition as used in ozone exposure experiment except that Vitamin E level is 0.15 wt %, a similar experiment is conducted using cumene hydroperoxide as the oxidant challenge. Below are the results:

TABLE 6

LPO Levels for Vitamin Treated versus Untreated Skin after Cumene Hydroperoxide Exposure

| Skin Treatment | LPO percent Neutralized |
|---|---|
| Untreated Control | 0 |
| Vehicle Only | 7 |
| Composition with Vitamin E and E Acetate | 51 |

Utilizing the cumene hydroperoxide system, predeposited vitamin provides at least 44 percent protection against the LPO.

Vitamin E Deposition on Skin from Topical Composition Provides More Vitamin E on Skin than Ingesting Oral Composition Containing Vitamin E.

Preparation 1 is used in the experiments following—Vitamin B is 0.15 wt %; Vitamin E acetate is at 0.10 wt %.

A. Test Method

Twenty-one (21) panelists above the age of 18 participate in this study.

Ten (10) subjects are in the Dietary group.

Eleven (11) subjects are in Topical group.

To standardize Vitamin E exposure, both groups are asked to refrain from taking vitamin supplementation and using skin care products containing Vitamin E. To ensure that the volunteers will not use vitamin-containing products, they are provided with body washes, lotion and a shampoo that the subjects return to a test facility.

Following the sampling procedure, the subjects in the dietary group are given a 400 IU (13XRDI) Vitamin B tablet and have both forearms washed with a shower gel lacking the Vitamin E and acetate precursor. The topical group has both forearms washed with the shower gel containing Vitamin E and Vitamin E acetate. This procedure is repeated each working day for a total of 9 working days for the topical and dietary group.

On day 9, immediately after the final wash and Vitamin E tablet administration, samples of skin are collected from each subject and analyzed for Vitamin E using the following procedures: A technician places a hollow glass cylinder (4.91 cm$^2$) on the skin surface and pipettes 1 ml of ethyl alcohol (dehydrated alcohol-200 Proof). The ethyl alcohol is allowed to contact the skin for 1 minute. After stirring with a glass rod, the extract is removed. This procedure is repeated for three more times to give a total of four extractions. The contents of the four extractions are pooled and analyzed for Vitamin E and Vitamin E Acetate.

B. Results

The results demonstrate that the skin shows substantially more Vitamin E deposits from a topical administration of vitamin than oral administration of a Vitamin E tablet of 400 I.U. (13 times more than recommended dietary intake), as shown in the Table below:

TABLE 7

| Composition | Vitamin E Picomoles/cm$^2$ Skin ± standard error |
|---|---|
| Untreated | 10 ± 1 |
| Topical | 267 ± 8 |
| Dietary | 78 ± 11 |

This data clearly show how appropriate topical skin treatment is actually more effective in providing significant levels of antioxidant in the skin in comparison to classical oral system delivery of vitamins.

In summation, the three effects observed here are unusual. The long-lasting effect of the topical composition, at least 6 hours, desirably at 15 hours, and even more desirably 24 hours or more, the ability of predeposited antioxidant vitamin to inhibit at least about 30 percent of LPO, desirably at least about 40 or 50% of LPO generated after an insult to the skin, and the ability of topical composition to provide a higher level of vitamin on skin than oral ingestion of vitamin provides, even at very high levels of oral ingestion, are indeed noteworthy.

What is claimed is:

1. An aqueous liquid or gel topical rinse off composition for cleansing the skin wherein the composition comprises:
   (a) a cleansing amount of at least one surfactant which is selected from the group consisting of anionic, nonionic, amphoteric and cationic surfactants;
   (b) a minimum of about 0.05 weight % of Vitamin E based on the weight of the composition;
   (c) a minimum of about 0.03 weight % of a Vitamin E precursor based on the weight of the composition so that the ratio of Vitamin E to Vitamin E precursor is in the range of from about 1 to about 3 to about 3 to about 1; and
   (d) a stabilizing amount of a cationic polymer which is at least about 0.01 weight % of the composition;
   whereby application of the composition results in at least one of the following effects:
   (i) inhibition of at least about 30% of lipid peroxide level generated after an insult to a skin area treated with the composition and exposed to said insult; or
   (ii) an elevated level of Vitamin E on skin treated with the composition which is significantly above the amount of Vitamin E on skin untreated with the composition, and which elevated level continues for a period of at least fifteen hours after application of the composition; or
   (iii) a level of Vitamin E on the skin which is significantly above the level obtained by oral ingestion of Vitamin E.

2. The composition in accordance with claim 1 wherein the Vitamin E precursor is an ester of Vitamin E, the ester having an alkyl group of one to twenty carbon atoms.

3. The composition in accordance with claim 2 wherein the precursor is Vitamin E acetate.

4. The composition in accordance with claim 1 wherein the insult is exposure to ozone.

5. The composition in accordance with claim 1 wherein the amount of Vitamin E in the composition is a minimum of about 0.1 weight %.

6. The composition in accordance with claim 1 wherein the amount of Vitamin E precursor in the composition is a minimum of about 0.04 weight %.

7. The composition in accordance with claim 1 or 5 wherein the maximum amount of Vitamin E in the composition is about 3 weight %.

8. The composition in accordance with claim 1 or 6 wherein the maximum amount of Vitamin E precursor in the composition is about 9 weight %.

9. The composition of claim 1 wherein the maximum amount of cationic polymer is about 2 weight %.

10. The composition of claim 1 wherein the cationic polymer is selected from the group consisting of:
    (a) cationic polysaccharides;
    (b) cationic copolymers of saccharides and synthetic cationic monomers; and
    (c) synthetic polymers selected from the group consisting of:
        (i) cationic polyalkylene imines;
        (ii) cationic ethoxy polyalkylene imimes;
        (iii) cationic poly[N-[3-(dimethylammonio)propyl]-N'[3-(ethyleneoxy-ethylene dimethylammonio)propyl] urea dichloride]; and
        (iv) polymers having a quaternary ammonium or substituted ammonium ion.

11. The composition of claim 1 wherein the anionic surfactant is an anionic non-soap surfactant selected from the group consisting of alkali metal salts of organic sulfates having an alkyl radical of from about 8 to about 22 carbon atoms and a sulfonic acid or sulfuric acid ester radical.

12. The composition of claim 11 wherein the anionic non-soap surfactant is selected from the group consisting of sodium, ammonium, potassium and triethanolamine alkyl sulfates; sodium coconut oil fatty acid monoglyceride sulfates and sulfonates; sodium and potassium salts of sulfuric acid esters formed as reaction products of 1 mole of a tallow or coconut oil alcohol and 1 to 12 moles of ethylene oxide; sodium and potassium salts of alkyl phenol ethylene oxide ether sulfate with 1 to 10 units of ethylene oxide per molecule and in which the alkyl radicals contain from 8 to 12 carbon atoms; sodium alkyl glyceryl ether sulfonates; reaction products of fatty acids having from 10 to 22 carbon atoms esterified with isethionic acid and neutralized with sodium hydroxide; and water soluble salts of condensation products of fatty acids with sarcosine.

* * * * *